(12) United States Patent
Felding et al.

(10) Patent No.: US 7,494,590 B2
(45) Date of Patent: Feb. 24, 2009

(54) METHOD OF CONTROLLING A DIALYSIS APPARATUS

(75) Inventors: Anders Felding, Limhamn (SE); Jan Sternby, Lund (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 10/491,427

(22) PCT Filed: Oct. 1, 2002

(86) PCT No.: PCT/SE02/01785

§ 371 (c)(1),
(2), (4) Date: Oct. 22, 2004

(87) PCT Pub. No.: WO03/028860

PCT Pub. Date: Apr. 10, 2003

(65) Prior Publication Data

US 2005/0061740 A1    Mar. 24, 2005

(30) Foreign Application Priority Data

Oct. 2, 2001    (SE) .................................... 0103290

(51) Int. Cl.
*B01D 61/32* (2006.01)
*B01D 61/28* (2006.01)
(52) U.S. Cl. ............... 210/646; 210/85; 210/87; 210/97; 210/103; 210/252; 210/258; 210/321.6; 210/321.65; 210/645; 210/650; 210/739; 210/741; 210/742; 604/4.01; 604/5.01; 604/6.09; 604/6.11; 604/9

(58) Field of Classification Search ........... 210/85, 210/87, 97, 103, 134, 143, 252, 258, 321.6, 210/321.65, 645, 646, 650, 739, 741, 742; 604/4.01, 5.01, 6.09, 6.11, 9
See application file for complete search history.

(56) References Cited

U.S. PATENT DOCUMENTS

| | | | | |
|---|---|---|---|---|
| 4,370,983 A * | 2/1983 | Lichtenstein | ............... | 600/301 |
| 4,381,999 A * | 5/1983 | Boucher et al. | ............ | 210/637 |
| 4,464,172 A * | 8/1984 | Lichtenstein | ................. | 604/65 |
| 4,708,802 A * | 11/1987 | Rath et al. | ................. | 210/641 |
| 4,710,164 A * | 12/1987 | Levin et al. | ................. | 604/66 |
| 4,711,715 A * | 12/1987 | Polaschegg | ................ | 210/103 |
| 4,739,492 A | 4/1988 | Cochran | | |
| 4,897,184 A * | 1/1990 | Shouldice et al. | ............ | 210/87 |
| 4,923,598 A * | 5/1990 | Schal | ........................ | 210/87 |
| 4,990,258 A * | 2/1991 | Bjare et al. | ................ | 210/647 |
| 5,276,611 A | 1/1994 | Ghiraldi | | |
| 5,366,630 A | 11/1994 | Chevallet | | |

(Continued)

FOREIGN PATENT DOCUMENTS

EP    0 722 744 A1    7/1996

(Continued)

*Primary Examiner*—John Kim
(74) *Attorney, Agent, or Firm*—Finnegan, Henderson, Farabow, Garrett & Dunner, L.L.P.

(57) ABSTRACT

The present invention relates to a method of controlling a dialysis apparatus, which can be used, e.g., for hemodialysis, hemodiafiltration, or hemofiltration. Numerous alarms occur during treatments creating additional workloads for the operator. The present method of controlling the apparatus allows an automatic switch from a first control mode to another, thus allowing the treatment to continue without operator influence.

18 Claims, 2 Drawing Sheets

U.S. PATENT DOCUMENTS

| | | |
|---|---|---|
| 5,762,805 A * | 6/1998 | Truitt et al. .................. 210/645 |
| 5,792,367 A * | 8/1998 | Mattisson et al. ........... 702/100 |
| 6,284,131 B1 | 9/2001 | Hogard et al. |
| 6,471,872 B2 * | 10/2002 | Kitaevich et al. ........... 210/739 |
| 6,554,789 B1 * | 4/2003 | Brugger et al. ............ 604/6.11 |
| 6,602,424 B1 * | 8/2003 | Kramer et al. .............. 210/739 |
| 6,767,333 B1 * | 7/2004 | Muller et al. .............. 604/6.09 |
| 6,780,322 B1 * | 8/2004 | Bissler et al. ............... 210/637 |

FOREIGN PATENT DOCUMENTS

WO　　WO 80/02376　　11/1980

\* cited by examiner

METHOD OF CONTROLLING A DIALYSIS APPARATUS

TECHNICAL FIELD

The present invention relates to a method of controlling a dialysis apparatus, which can be used for e.g. hemodialysis, hemodiafiltration or hemofiltration.

BACKGROUND ART

U.S. Pat. No. 5,366,630 discloses a method of controlling a dialysis apparatus for hemofiltration treatment by establishing the positive transmembrane pressure (TMP) between first and second compartments of a dialyser having two compartments separated by a semi permeable membrane, the first compartment being connected to a blood circuit for conveying blood outside of a human body and the second compartment having an inlet connectable to dialysate liquid circuit. The value of the TMP is measured and compared with a threshold value. When the measured value is greater than the threshold value treatment liquid is supplied to the inlet of the second compartment the exchanger and effectively the treatment mode is switched from hemofiltration to hemodiafiltration.

The Gambro AK 200 ULTRA™ online dialysis machine can be controlled in a number of different modes of operation of which the two most relevant modes will be discussed here. Before the treatment is started, the desired weight loss of the patient is determined, and is divided by the treatment time in order to get a desired weight loss rate. In a first mode of operation, usually referred to as "volume control", the desired total replacement volume is divided by a treatment time to get the infusion rate. The pump for the replacement fluid is set to deliver fluid at this desired rate. The fluid balancing system will compensate for the amount of replacement fluid. A certain TMP will result, depending on the characteristics of the membrane and the blood composition. Thus, a predetermined amount of fluid is ultrafiltered to the dialyser and the correct weight loss of the patient is reached at the end of the treatment time. In another mode of operation, usually referred to as "pressure control", a desired TMP is set in order to achieve a high ultrafiltration rate higher than the desired weight loss rate. Often this TMP set point is chosen close to the maximum TMP allowed. The chosen TMP will resolve in a certain ultrafiltration rate, which will depend on the blood composition and characteristics, i.e. permeability of the chosen dialyser. The resulting ultrafiltration will determine the infusion flow rate that has to be produced by the apparatus. The treatment is stopped when the accumulated ultrafiltration liquid volume reaches the predetermined value.

These two methods for control can each under certain circumstances produce alarms because some threshold values are exceeded. In order to shorten the length of the treatment in volume control, it is desirable to set the infusion rate as high as possible. It is however difficult to know exactly the limits set by the filtering capacity of the dialyser. In addition, as the treatment progresses and the blood becomes thicker due to the accumulating weight loss, this filtering capacity will gradually decrease. The result is frequently that the infusion rate is set at a value which may work at the start, but as the treatment progresses there is an increasing number of TMP alarms due to insufficient filtering capacity.

There is a similar situation in pressure control. If the TMP is set too close to the maximum allowable TMP, the resulting ultrafiltration rate may become so high that the necessary replacement fluid rate cannot be achieved by the pump. This will create an alarm situation.

DISCLOSURE OF THE INVENTION

On this background, it is the object of the present invention to provide a method of controlling a hemodialysis, a hemodiafiltration or hemofiltration treatment of the kind referred to initially, which overcomes the above-mentioned problem. This object is achieved by switching to controlling another process parameter.

According to an embodiment of the invention the controlled parameter is controlled so as to maintain a predetermined value or follow a predetermined profile.

In a further embodiment, the dialysis apparatus is suitable for hemodialysis, and/or hemodiafiltration, and/or hemofiltration. The control parameters preferably comprise TMP, and/or ultrafiltrate liquid flow rate, and/or replacement fluid flow rate.

According to yet another embodiment the method comprises the step of selecting an initial parameter to be controlled, if a switch from controlling said initial parameter to controlling another parameter has taken place, returning to said initial control parameter after a predetermined time span since said switch.

Further objects, features, advantages and properties of the method of controlling a hemodialysis, a hemodiafiltration or hemofiltration treatment according to the invention will become apparent from the detailed description.

BRIEF DESCRIPTION OF THE DRAWINGS

In the following detailed portion of the present description, the invention will be explained in more detail with reference to the exemplary embodiments shown in the drawings, in which.

DETAILED DESCRIPTION

Figure 1:
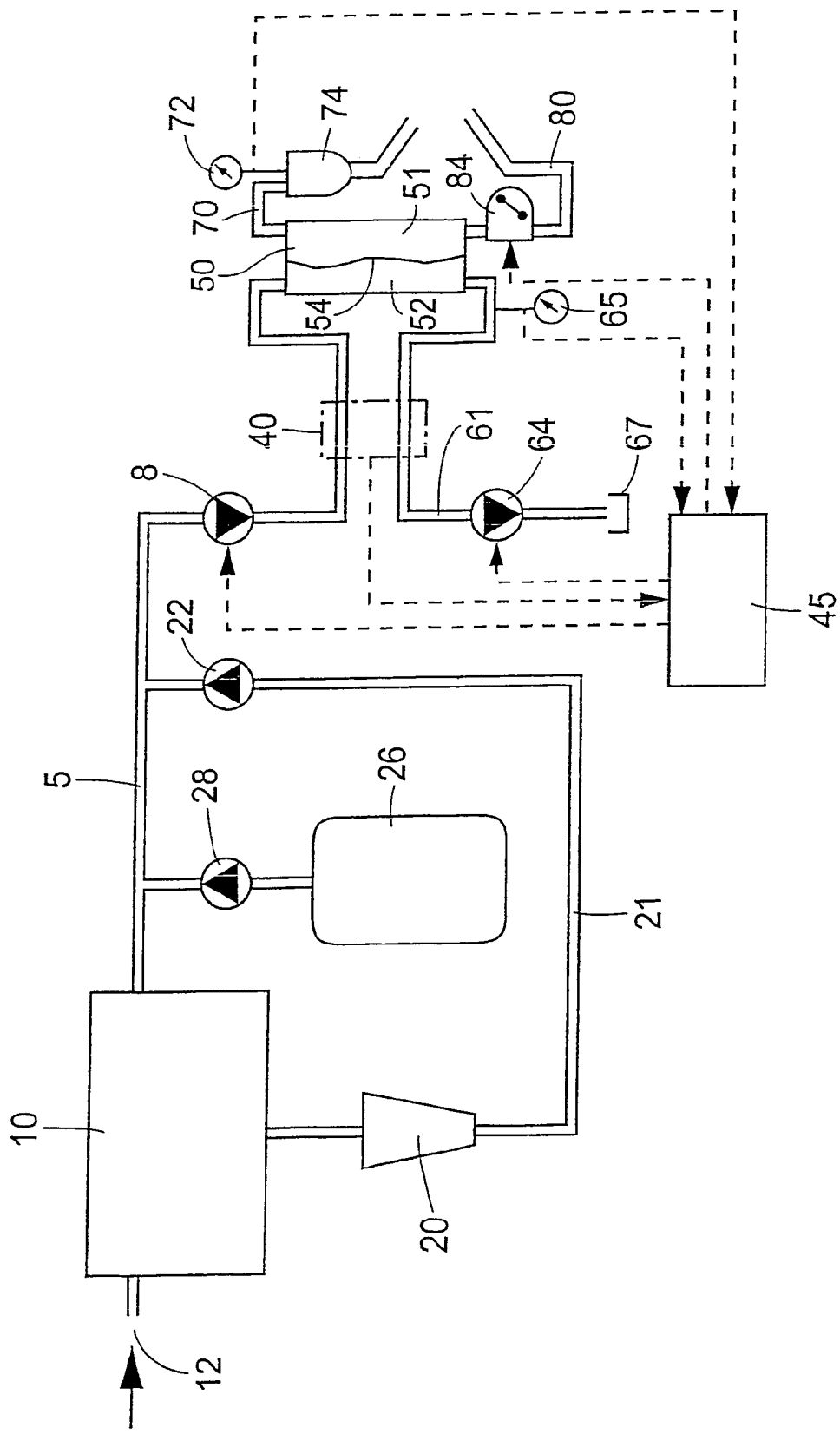
FIG. 1 is a diagrammatic view of a first preferred embodiment of the invention.

In FIG. 1, a dialysis apparatus according to a first preferred embodiment of the invention includes a dialyser 50 having two compartments 51 and 52 that are separated by a semi permeable membrane 54. The compartment 51 is connected to a circuit for convening a flow of blood outside the body of a patient comprising an upstream duct 80, having a peristaltic pump 84 disposed therein, and a downstream duct 70. Duct 70 is provided with a bubble trap 74 and the free ends of the ducts are fitted respective needles or catheter connections to enable them to be connected to the vascular circuit of a patient.

A system for preparing dialysate from dialysate concentrate and powder comprises a tank 10 having an inlet 12 for water from for example a reversed osmosis unit, a dry powder cartridge 20 containing bicarbonate is disposed in duct 21. A part of the heating reservoir 10 is flown through the cartridge 20 by a precisely controlled pump 22. The dialysate preparation system further comprises a main duct 5 to which the so-called "A-concentrate" is added by withdrawing it from a canister 26 by means of a pump 28. The main duct includes a pump 8 and directs the dialysate to an inlet of compartment 52 of the dialyser 50. An outlet of the compartment 52 is connected to a downstream duct 61 having an extraction pump 64 disposed therein for establishing variable suction inside the compartment 52. The duct 61 leads to a waste liquid (ultrafiltrate and/or waste dialysis liquid) container 67. Duct 5 leading to compartment 52 and duct 61 leading away from compartment 52 both pass a flow rate cell 40. The flow rate cell 40 generates a signal indicative of the difference in flow rate between the incoming dialysate and the outgoing ultrafiltrate and waste dialysis liquid. The signal is therefore indicative of the ultrafiltration flow rate. A control unit 45 receives the signal from the flow rate cell 40 and operates in a manner of explained below to control the flow rate of pumps 8, 64 and 84. In this manner the control unit 45 can adjust the ultrafiltration flow rate and the TMP. Before describing the operation on this dialysis apparatus a brief comment on the hemodialysis treatment follows. The flow rate of ultrafiltrate through a dialyser membrane is a function of the pressure difference (the transmembrane pressure) that exist between the two compartments of the dialyser. Before a treatment the desired weight loss of the patient is determined, and divided by the treatment time in order to get a desired weight loss rate.

In the light of the above, the dialysis apparatus of the invention operates on the following principles. Before the beginning of a treatment session, an operator stores in the memory of the control unit 45 both a desired reference blood flow rate QB and a desired weight loss rate QWL as prescribed by the medical doctor (or as derived from a total desired weight loss prescribed by the medical doctor) (were QWL is equal by definition to the ultrafiltration flow rate). In accordance with a correspondence relationship previously stored in its memory, the control unit automatically associates the blood flow rate QB with an upper threshold value TMP 1 and a lower threshold value TMP 2 for the transmembrane pressure specific to the dialyser 50 being used. After initial rinsing and filling of the ducts and after the circuit for convening a flow of blood outside the body has been connected to the vascular circuit of the patient, the pumps 8, 64 and 84 are adjusted to a constant flow rate. Two different modes of control can now be selected for the initial control. If the ultrafiltration rate is selected as the control parameter, the flow rate of pump 64 is controlled to a value which corresponds to the flow rate value of pump 8 added with the desired ultrafiltration flow rate. In order to perform this control the dialysis apparatus disposes over a control loop formed by the flow rate cell 40 that generates a signal to the control unit 45. The control unit 45 generates a control signal to both pumps 64 and 8 to adjust their performance to achieve exactly the desired ultrafiltration flow rate. The desired ultrafiltration flow rate is usually constant and stored in the control unit 45, but alternatively the ultrafiltration flow rate may follow a profile stored in the control unit. The resulting TMP depends on the characteristics of the selected membrane and the blood composition. The resulting TMP is monitored by using the pressure of the dialysate downstream of the dialyser 50 indicated by sensor 65 which generates a signal that is sent to the control unit 45 and the pressure sensor 72 which produces a signal indicative of the blood pressure downstream of the dialyser 50 and sends a corresponding signal to the control unit 45. If the measured value of TMP is outside the allowable range, i.e. either above the upper threshold or below the lower threshold, the control unit will switch to controlling the TMP by controlling the pumps 8, 64 and 84 in response to the measured TMP. The TMP will be controlled so as to maintain a predetermined value stored in the control unit 45 or in accordance with a profile stored in a control unit 45. The resulting ultrafiltration flow rate depends on the characteristics of the membrane and the blood composition and will be monitored by the flow rate cell 40.

The treatment may also start in the TMP control mode. If the ultrafiltration flow rate exceeds its threshold, the control unit 45 will switch to controlling the ultrafiltration flow rate. According to a preferred embodiment the control is switched back to the initial in the control parameter after a time stored in control unit 45.

Figure 2:
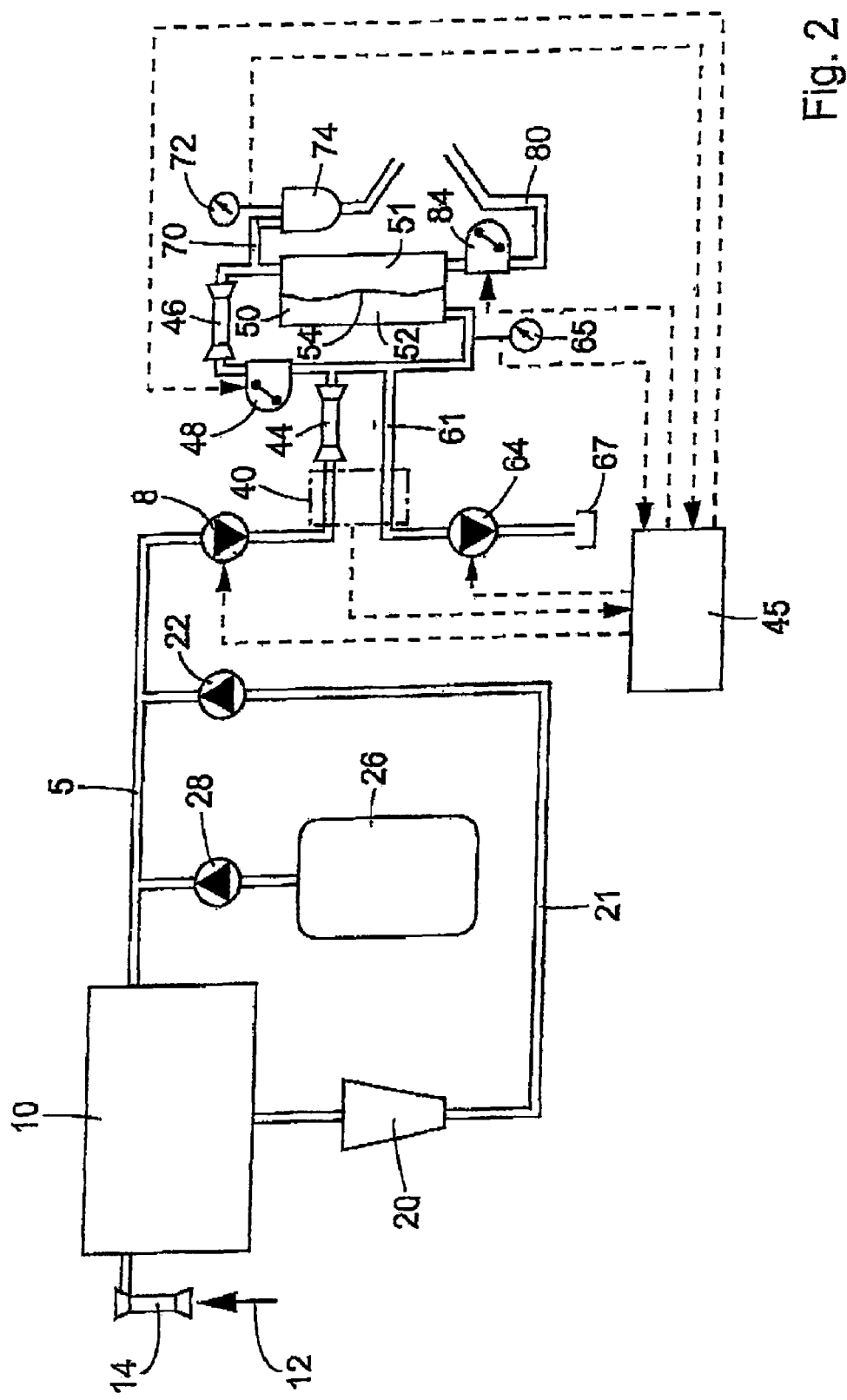
FIG. 2 is a diagrammatic view of another preferred embodiment of the invention

FIG. 2 shows a second embodiment of the invention, which is particularly suitable for carrying out a hemofiltration treatment. It has in common with first embodiment most of its circuits for convening blood outside the body and it circuits for dialysate and waste liquids. It differs there from in that it comprises means for providing sterile replacement fluid for the patient. Therefore it comprises in addition to the system of the first embodiment a first ultrafilter 14 which is placed in the inlet duct 12. A second ultrafilter 44 is placed in the main duct 5 after the flow rate cell 40. Downstream of the second ultrafilter 44 the main duct splits in a branch leading to the waste liquid duct 61 and another branch continuing towards the extracorporeal blood flow for delivering replacement fluid to the patient. A third ultrafilter 46 is placed in the branch delivering the replacement fluid. The three ultrafilters in series guarantee a sufficient sterile quality of the replacement fluid. Fewer ultrafilters may be used, however with an increased risk of insufficient sterility of the replacement fluid.

Further a replacement fluid pump 48 is placed in the branch delivering the replacement fluid to the patient. The replacement fluid is mixed with the patient blood at a mixing point 58 in the downstream duct 70.

The flow rate of the replacement fluid pump 48 determines the amount of replacement fluid delivered to the patient. The flow rate cell 40 generates a signal indicative of the difference in flow rate between the incoming replacement fluid and the outgoing ultrafiltrate and waste replacement fluid. The signal is therefore indicative of the weight loss rate of the patient. The ultrafiltration flow rate, which is in hemofiltration unlike in hemodialysis, not equal to the weight loss rate, but determined by adding the replacement fluid rate to the weight loss rate. A control unit 45 receives the signal from the flow rate cell 40 and operates in a manner of explained below to control the flow rate of pumps 8, 64 and 84. The control unit 45 also steers the flow rate of the replacement fluid pump 48. In this manner the control unit 45 can adjust the ultrafiltration flow rate and the TMP. Before describing the operation on this dialysis apparatus a brief comment on the hemofiltration treatment follows. The flow rate of ultrafiltrate through a dialyser membrane is a function of the pressure difference (the transmembrane pressure) that exists between the two compartments of the dialyser. Before a treatment the desired weight loss of the patient is determined, and divided by the treatment time in order to get a desired weight loss rate. The total treatment is determined by the total ultrafiltrate volume and the weight loss of the patient.

The dialysis apparatus according to the second embodiment of the invention operates on the following principles. Before the beginning of a treatment session, an operator stores in the memory of the control unit 45 a desired reference blood flow rate QB, a desired treatment time, a derived desired weight loss rate QWL, and the ultrafiltration flow rate and replacement fluid flow rate as prescribed by the medical doctor (where QWL is equal by definition to the difference at any instant between the ultrafiltration flow rate and the replacement fluid flow rate). In accordance with a corresponding relationship previously stored in the memory of the control unit, the control unit 45 automatically associates the blood flow rate QB with an upper threshold value $TMP_1$ and a lower threshold value $TMP_2$ for the transmembrane pressure specific to the dialyser 50 being used. After initial rinsing and filling of the ducts and after the circuit for conveying a flow of blood outside the body has been connected to the vascular circuit of the patient, the pumps 8, 64, and 84 are adjusted to a constant flow rate. Two different modes of control can now be selected for the initial control. If the ultrafiltration rate is selected as the control parameter, the flow rate of pump 64 is controlled to a value which corresponds to the flow rate value of pump 8 added with the desired ultrafiltration flow rate. In order to perform this control the dialysis apparatus disposes over a control loop formed by the flow rate cell 40 that generates a signal to the control unit 45. The control unit 45 generates a control signal to both pumps 64 and 8 to adjust their performance to achieve exactly the desired ultrafiltration flow rate. The desired ultrafiltration flow rate is usually constant and stored in the control unit 45, but alternatively the ultrafiltration flow rate may follow a profile stored in the control unit. The resulting TMP depends on the characteristics of the selected membrane and the blood composition. The resulting TMP is monitored by using the pressure of the dialysate downstream of the dialyser 50 indicated by sensor 65 which generates a signal that is sent to the control unit 45 and the pressure sensor 72 which produces a signal indicative of the blood pressure downstream of the dialyser 50 and sends a corresponding signal to the control unit 45. If the measured value of TMP is outside the allowable range, i.e., either above the upper threshold or below the lower threshold, the control unit will switch to controlling the TMP by controlling the pumps 8, 64 and 84 in response to the measured TMP. The TMP will be controlled so as to maintain a predetermined value stored in the control unit 45 or in accordance with a profile stored in a control unit 45. The resulting ultrafiltration flow rate depends on the characteristics of the membrane and the blood composition and will be monitored by the flow rate cell 40.

The treatment may also start in the TMP control mode. The control unit 45 regulates the pumps 8, 64 and 84 so as to maintain the set TMP. This setting results in a certain ultrafiltration flow rate. The control unit derives from the ultrafiltration flow rate and the desired weight loss rate a required replacement fluid rate. If this required amount of replacement fluid is exceeds its threshold, the control unit 45 will switch to controlling the replacement fluid flow rate instead.

According to a preferred embodiment the control unit 45 switches back to controlling the initial control parameter after a switch has taken place. The return to controlling the initial control parameter is performed after a predetermined time set or stored in control unit 45 or when the initial control parameter has returned below its threshold or a return-threshold.

The general term dialysis as used here includes hemodialysis, hemofiltration, hemodiafiltration and therapeutic plasma exchange (TPE), among other similar treatment procedures. The general term "dialyser" as used here includes hemofilters, ultrafilters, and hemodiafilters.

The general term "means for measuring transmembrane pressure" as used here includes any conventional pressure transducers or sensors, which in general measure the pressures from the venous line of the extracorporealblood circuit, and the dialysis fluid downstream from the dialyser. From these measurements an estimate of the transmembrane pressure is derived. It is also possible to measure the pressure both before and after the dialyser in the dialysate flow path and in the blood flow path and derive an estimate of the transmembrane pressure from these four measurements.

The general term "means for measuring the volume or ultrafiltration flow rate" as used here includes flow meters of coreolis (mass flow), turbine, orifice nozzle, venturi flow or electromagnetic induction (Faradays law) type. The ultrafiltration flow rate can be determined by comparing signals from two meters, one for incoming dialysate and one for waste liquid, or the flow meters may be of the differential type that gives one signal representative of the ultrafiltration flown rate. If the dialysis apparatus uses the balance chamber system for the transport of dialysate, it is not always necessary to use differential flow meters. Instead the flow can be derived from the speed of the ultrafiltrate pump used in the balance chamber system, or by simply collecting the waste liquid and measuring it by weight or volume.

The invention is not limited to the two exemplary embodiments described above, and variants may be provided. The preparation of the fluids does not have to be as described online. Instead ready mixed fluids from e.g. pre-packaged bags of sterile replacement fluid, which will also do away with the need for ultrafilters, may be used.

In general, the threshold values for the purpose of switching the control parameter may be different from, values at which the dialysis machine will activate an alarm to warn the operator. Therefore, the present invention will normally reduce the number for alarms that occur regularly in certain circumstances, but will not do away with the alarms altogether.

Although the dialysis apparatus has been described with a sensor measuring the flow rate in the main duct, measuring flow rate in the waste liquid duct, and determining the ultrafiltrate flow rate by comparing the two measured flow rates, the dialysis apparatus can be modified to the so called "double chamber principle," which is well known in the art. The apparatus can also perform hemodiafiltration treatment, in which the branch of the main duct leading to the waste duct is in a well-known manner connected to the inlet of the dialyser. Several parameters have been described as control parameters, other parameters of the apparatus could also be used, e.g., the TMP and the treatment time could be fixed whereas the total ultrafiltrate volume will depend on the resulting accumulated ultrafiltrate flow rate. According to another embodiment, the dialysate flow rate could be controlled instead of the replacement fluid rate when the incoming (cold) water flow exceeds the heating capacity of the monitor. The maximum heating capacity of the heating reservoir 10 can in particular under circumstances with relatively cold incoming water be exceeded. In a conventional dialysis apparatus first an alarm with be set and eventually the machine will be stopped. According to this embodiment, the machine will switch to controlling the dialysate flow rate and limit the flow rate to the heating capacity of the heating element. Thus, the apparatus can continue the treatment.

In another embodiment the blood pressure in the extracorporeal circuit and the blood flow rate in the extracorporeal circuit are used as parameters to switch between. Normally desired blood flow rate is set at the start of the treatment. The control unit 45 regulates the peristaltic pump 84 in accordance with the desired blood flow rate. The chosen blood flow rate results under certain circumstances in unacceptable blood pressures e.g. too high blood pressure before the dialyser or too low blood pressure before the pump. These occurrences give rise to alarms in conventional dialysis machines. In this embodiment of the invention, the control unit will switch form controlling the blood flow rate controlling the blood pressure control when a blood pressure threshold is exceeded. The control unit will thus regulate the peristaltic pump in accordance with a preset value of the blood pressure stored in the control unit 45. When the blood pressure regains a normal value, the apparatus may switch back after a predetermined time to the blood flow rate control.

The above-described different embodiments can be combined in a single apparatus. Thus the apparatus could both have automatic switching between transmembrane pressure/replacement fluid rate control and between blood pressure/blood flow control.

LIST OF REFERENCE NUMERALS

5 Main duct
8 Pump
10 Heating reservoir
12 Inlet
14 $1^{st}$ Ultrafilter
20 Bicarbonate cartridge
21 Duct
22 Pump
26 A-concentrate container
28 Pump
40 Flow rate cell
44 $2^{nd}$ Ultrafilter
46 $3^{rd}$ Ultrafilter
45 Control unit
48 Replacement fluid pump
50 Dialyser
51 First compartment
52 Second compartment
54 Membrane
61 Waste liquid duct
64 Extraction pump
65 Pressure sensor
67 Waste liquid container
70 Downstream duct
72 Pressure sensor
74 Bubble trap
80 Upstream duct
84 Peristaltic pump

The invention claimed is:

1. A method of controlling a dialysis apparatus comprising the steps of:
observing at least two parameters related to the dialysis, the at least two parameters including at least two of the following parameters: transmembrane pressure, ultrafiltration flow rate, replacement fluid flow rate, blood pressure, blood flow rate, dialysate flow rate, and dialysate temperature;
determining a range of acceptable values for said at least two parameters;
controlling one of said at least two parameters; and
switching to controlling one of the other of said at least two parameters when one of the other of said at least two parameters is outside the respective range of acceptable values, wherein said steps of observing, determining, controlling, and switching all occur during a particular treatment mode, and without switching to an alternative treatment mode.

2. A method according to claim 1, wherein the controlled parameter is controlled so as to maintain a predetermined value or follow a predetermined profile.

3. A method according to claim 1 or 2, wherein said particular treatment mode is one of hemodialysis, hemodiafiltration, and hemofiltration.

4. A method according to claim 1, wherein said at least two parameters comprise transmembrane pressure and ultrafiltration flow rate.

5. A method according to claim 1, wherein said at least two parameters comprise transmembrane pressure and replacement fluid flow rate.

6. A method according to claim 1, wherein said at least two parameters comprise blood pressure and blood flow rate.

7. A method according to claim 1, wherein said at least two parameters comprise dialysate flow rate and dialysate temperature.

8. A method according to claim 1, comprising the step of selecting an initial parameter to be controlled, if a switch from controlling said initial parameter to controlling another parameter has taken place, returning to said initial control parameter after a predetermined time span since said switch or when the initial control parameter has returned below a threshold or other predetermined value.

9. A method of controlling a dialysis apparatus comprising the steps of:
causing the flow of blood on one side of a semi permeable membrane;
causing the flow of dialysate at the other side of said semi permeable membrane;
observing the transmembrane pressure;
observing the ultrafiltration flow rate
defining a threshold value for the transmembrane pressure;
defining a threshold value for the ultrafiltration flow rate;
controlling either the transmembrane pressure or the ultrafiltration flow rate so as to maintain a predetermined value or follow a predetermined profile, switching from controlling transmembrane pressure to controlling ultrafiltration flow rate, when the ultrafiltration flow rate threshold is exceeded and switching from controlling ultrafiltrate flow rate to controlling transmembrane pressure when the transmembrane pressure threshold is exceeded, wherein said steps of observing, determining, controlling, and switching all occur during a particular treatment mode, and without switching to an alternative treatment mode.

10. A method of controlling a dialysis apparatus comprising the steps of:
causing the flow of blood on one side of a semi permeable membrane;
causing the flow of dialysate at the other side of said semi permeable membrane;
providing replacement fluid at a certain rate;
observing the transmembrane pressure;
observing the replacement fluid rate;
defining a threshold value for the transmembrane pressure;
defining a threshold value for the replacement fluid rate;
controlling either the transmembrane pressure or the replacement fluid rate so as to maintain a predetermined value or follow a predetermined profile, switching from controlling transmembrane pressure to controlling replacement fluid rate, when the replacement fluid flow rate threshold is exceeded; and
switching from controlling replacement fluid flow rate to controlling transmembrane pressure when the transmembrane pressure threshold is exceeded,
wherein said steps of observing, determining, controlling, and switching all occur during a particular treatment mode, and without switching to an alternative treatment mode.

11. An apparatus for hemodialysis, hemodiafiltration, or hemofiltration comprising:
a dialysate flow path;
a blood flow path;
a dialyser having a semi permeable membrane;
a first compartment on one side of said semi permeable membrane coupled to said dialysate flow path and a second compartment on another side of said membrane coupled to said blood flow path;

means for measuring the transmembrane pressure;
means for measuring the volume or flow rate of ultrafiltration liquid;
means for regulating the transmembrane pressure, means for regulating the ultrafiltration flow rate;
control means for selectively controlling either transmembrane pressure or ultrafiltration flow rate;
means for setting and storing threshold values for transmembrane pressure and ultrafiltration flow rate;
selection means for switching from controlling transmembrane pressure to controlling ultrafiltration flow rate when the ultrafiltration flow rate threshold is exceeded; and
means for switching from controlling ultrafiltration flow rate to controlling transmembrane pressure when the transmembrane pressure threshold is exceeded.

12. An apparatus for hemodiafiltration or hemofiltration comprising:
a dialysate flow path;
a blood flow path;
a dialyser having a semi permeable membrane, a first compartment on one side of said semi permeable membrane coupled to said dialysate flow path and a second compartment on another side of said membrane coupled to said blood flow path;
means for measuring the transmembrane pressure;
means for providing a replacement fluid flow at a certain flow rate;
means for regulating the transmembrane pressure;
means for regulating the replacement fluid flow rate;
control means for selectively controlling either transmembrane pressure or replacement fluid flow rate;
means for setting and storing threshold values for transmembrane pressure and replacement fluid flow rate; and
selection means for switching from controlling transmembrane pressure to controlling replacement fluid flow rate when the replacement fluid flow rate threshold is exceeded and for switching from controlling replacement fluid flow rate to controlling transmembrane pressure when the transmembrane pressure threshold is exceeded.

13. A method according to claim 1, wherein the step of switching does not result in the activation of an alarm.

14. A method according to claim 1, wherein the step of switching does not result in a stoppage of a dialysis treatment.

15. A method according to claim 9, wherein the step of switching does not result in the activation of an alarm.

16. A method according to claim 9, wherein the step of switching does not result in a stoppage of a dialysis treatment.

17. A method according to claim 10, wherein the step of switching does not result in the activation of an alarm.

18. A method according to claim 10, wherein the step of switching does not result in a stoppage of a dialysis treatment.

* * * * *

UNITED STATES PATENT AND TRADEMARK OFFICE
CERTIFICATE OF CORRECTION

PATENT NO.         : 7,494,590 B2
APPLICATION NO. : 10/491427
DATED              : February 24, 2009
INVENTOR(S)        : Anders Felding et al.

It is certified that error appears in the above-identified patent and that said Letters Patent is hereby corrected as shown below:

In claim 3, column 7, line 61, "hemoflitration" should read --hemofiltration--.

In claim 9, column 8, line 20, insert semicolon after "rate".

Signed and Sealed this

Seventh Day of April, 2009

JOHN DOLL
*Acting Director of the United States Patent and Trademark Office*